United States Patent
Tang et al.

(10) Patent No.: US 11,450,004 B2
(45) Date of Patent: Sep. 20, 2022

(54) SYSTEM AND METHOD FOR AUTOMATIC RECOGNITION FOR HAND ACTIVITY DEFINED IN UNIFIED PARKINSON DISEASE RATING SCALE

(71) Applicant: TENCENT AMERICA LLC, Palo Alto, CA (US)

(72) Inventors: Hui Tang, Mountain View, CA (US); Yusheng Xie, Mountain View, CA (US); Shihyao Lin, Palo Alto, CA (US); Lianyi Han, Palo Alto, CA (US); Wei Fan, New York, NY (US)

(73) Assignee: TENCENT AMERICA LLC, Palo Alto, CA (US)

( * ) Notice: Subject to any disclaimer, the term of this patent is extended or adjusted under 35 U.S.C. 154(b) by 29 days.

(21) Appl. No.: 16/683,358

(22) Filed: Nov. 14, 2019

(65) Prior Publication Data

US 2021/0150718 A1 May 20, 2021

(51) Int. Cl.
| | | |
|---|---|---|
| *G06T 7/11* | (2017.01) | |
| *G06T 7/70* | (2017.01) | |
| *G06T 7/00* | (2017.01) | |
| *G06T 7/194* | (2017.01) | |
| *G06T 5/00* | (2006.01) | |

(Continued)

(52) U.S. Cl.
CPC ............... *G06T 7/11* (2017.01); *A61B 5/1101* (2013.01); *A61B 5/1128* (2013.01); *A61B 5/4082* (2013.01); *G06T 5/002* (2013.01); *G06T 7/0012* (2013.01); *G06T 7/194* (2017.01); *G06T 7/70* (2017.01); *A61B 5/0077* (2013.01); *A61B 2576/02* (2013.01); *G06T 2207/20081* (2013.01); *G06T 2207/20084* (2013.01); *G06T 2207/30004* (2013.01)

(58) Field of Classification Search
CPC . G06T 7/11; G06T 7/194; G06T 5/002; G06T 7/0012; G06T 2207/20081; G06T 2207/20084; G06T 2207/30004; G06T 7/12; G06T 2207/30196; A61B 5/1101; A61B 5/1128; A61B 5/4082; A61B 5/0077; A61B 2576/02; G06V 10/25; G06V 2201/03; G06V 10/40; G06V 40/20; G06V 40/113
See application file for complete search history.

(56) References Cited

U.S. PATENT DOCUMENTS

| | | |
|---|---|---|
| 8,600,166 B2 | 12/2013 | Adhikari |
| 2012/0119984 A1* | 5/2012 | Sankarasubramaniam ................. G06K 9/00926 345/156 |

(Continued)

OTHER PUBLICATIONS

"Fusion of Skin Color Detection and Background Subtraction for Hand Gesture Segmentation" S N Karishma, V Lathasree Rajiv Gandhi University of Knowledge Technologies, India (Year: 2014).*

(Continued)

*Primary Examiner* — Vu Le
*Assistant Examiner* — Winta Gebreslassie
(74) *Attorney, Agent, or Firm* — Sughrue Mion, PLLC (57) ABSTRACT

There is included an apparatus and system including image segmentation code, configured to cause at least one hardware processor to segment an image of a person's hand from an input image, and classification code configured to cause the at least one processor to classify the segmented image of the person's hand according to at least one predefined pose.

16 Claims, 9 Drawing Sheets

(51) Int. Cl.
    *A61B 5/11*    (2006.01)
    *A61B 5/00*    (2006.01)

(56) References Cited

U.S. PATENT DOCUMENTS

| | | | | |
|---|---|---|---|---|
| 2015/0077323 | A1* | 3/2015 | Ramaswamy | G06F 3/0304 |
| | | | | 345/156 |
| 2016/0089073 | A1 | 3/2016 | Tafazzoli et al. | |
| 2019/0122073 | A1 | 4/2019 | Ozdemir et al. | |
| 2020/0194117 | A1* | 6/2020 | Krieger | A61B 8/429 |
| 2020/0364868 | A1* | 11/2020 | Zhang | A61B 5/1101 |

OTHER PUBLICATIONS

International Search Report dated Nov. 27, 2020 from the International Searching Authority in International Application No. PCT/US2020/049856.

Written Opinion dated Nov. 27, 2020 from the International Searching Authority in International Application No. PCT/US2020/049856.

Olaf Ronneberger et al., "U-Net: Convolutional Networks for Biomedical Image Segmentation", Computer Science Department and BIOSS Centre for Biological Signalling Studies, University of Freiburg, Germany, May 18, 2015.

Jeff Donahue et al., "Long-term Recurrent Convolutional Networks for Visual Recognition and Description", 2015 IEEE Conference on Computer Vision and Pattern Recognition, pp. 2625-2634.

Du Tran et al., "Learning Spatiotemporal Features with 3D Convolutional Networks", 2015 IEEE International Conference on Computer Vision, pp. 4489-4497.

Li Yao et al., "Describing Videos by Exploiting Temporal Structure", 2015 IEEE International Conference on Computer Vision, pp. 4507-4515.

Christoph Feichtenhofer et al., "Convolutional Two-Stream Network Fusion for Video Action Recognition", Sep. 26, 2016.

* cited by examiner

SYSTEM AND METHOD FOR AUTOMATIC RECOGNITION FOR HAND ACTIVITY DEFINED IN UNIFIED PARKINSON DISEASE RATING SCALE

BACKGROUND

1. Field

The disclosed subject matter relates to activity recognition in the field of dyskinesias, such as in the hands of Parkinson's disease patients, including segmenting a hand from one or more images and further classifying a pose of the hand from the segmented image.

2. Description of Related Art

Conditions such as Parkinson's disease, or the like, may involve disorders of human motion. Various systems have been developed in attempt to detect aspects of the disorder, yet those systems are not always accessible nor precisely reproducible. For example, there is a Unified Parkinson's Disease Rating Scale (UPDRS) which may be used to evaluate a severity of Parkinson's disease. The UPDRS directs observation via a motor section involving measurement of dyskinesias such as in patients with Parkinson's disease or similar symptoms. Under the UPDRS, for example, different actions, five for example, related to a human hand may indicate different diagnostic elements regarding Parkinson's disease, yet, inter/intra observer variability may lead to different diagnostics of a same patient. Further, qualified observers for the purposes of UPDRS may not be easily available to patient unless available at a clinic or hospital.

Nonetheless, the related art has not developed systems for automatic detection, targeting user's at home or in medical facilities, of various criteria in quantifying such dyskinesias. For example, various background and illumination issues may arise in imaging various hand poses for diagnostic recognition during video capturing. That is, the background may contain other objects, other than the imaged hand, that are moving and which make such automatic recognition of dyskinesias a challenging task.

SUMMARY

As described above, although a hand may be imaged, the various background and illumination differences lead to challenges for hand pose recognition. To eliminate the influence of the background and illumination, exemplary embodiments of the present application describe artificial intelligence (AI) technology to first segment out the hand using deep learning and then feed a hand mask into a 3D convolutional neural network (CNN) classifier. The hand segmentation step is crucial since it removes the background from the video and focuses the following classification network onto the hands instead of the whole capture range of the raw image.

According to exemplary embodiments, there is described a method, a non-transitory computer-readable medium, and an apparatus comprising at least one memory configured to store computer program code, and at least one hardware processor configured to access said computer program code and operate as instructed by said computer program code where said computer program code includes image segmentation code, configured to cause the at least one hardware processor to segment an image of a person's hand from an input image, and classification code configured to cause the at least one processor to classify the segmented image of the person's hand according to at least one predefined pose.

According to exemplary embodiments, the at least one predefined pose comprises any of a hand tremor, a finger tapping, and a pronation-supination movement of the person's hand, and the image segmentation code is further configured to cause the at least one hardware processor to segment the image of the person's hand by extracting the person's hand from the input image such that a background, other than the person's hand, is removed from the input image.

According to exemplary embodiments, the image segmentation code is further configured to cause the at least one hardware processor to segment the input image of the person's hand by extracting the person's hand from the input image such that an illuminance removed from the input image, and the segmented image comprises a mask of the person's hand from the input image such that a background of the input image and an illuminance of the input image are removed from the input image.

According to exemplary embodiments, the computer program code further includes post processing code configured to cause the at least one hardware processor to smooth at least one edge of the person's hand in the segmented image, and the classification code is further configured to cause the at least one hardware processor to classify the segmented image in which the at least one edge has been smoothed according to the post processing code.

According to exemplary embodiments, the image segmentation code is further configured to cause the at least one hardware processor to segment the image according to a UNet segmentation network, the UNet segmentation network comprises data trained by manually labeled masks and at least one set of data augmentation techniques including any of histogram equalization, Gaussian blurring, rotation, and zoom techniques, and the classification code is further configured to cause the at least one hardware processor to classify the segmented image according to a convolutional neural network (CNN).

BRIEF DESCRIPTION OF THE DRAWINGS

Further features, nature, and various advantages of the disclosed subject matter will be more apparent from the following detailed description and the accompanying drawings in which.

DETAILED DESCRIPTION

Figure 1:
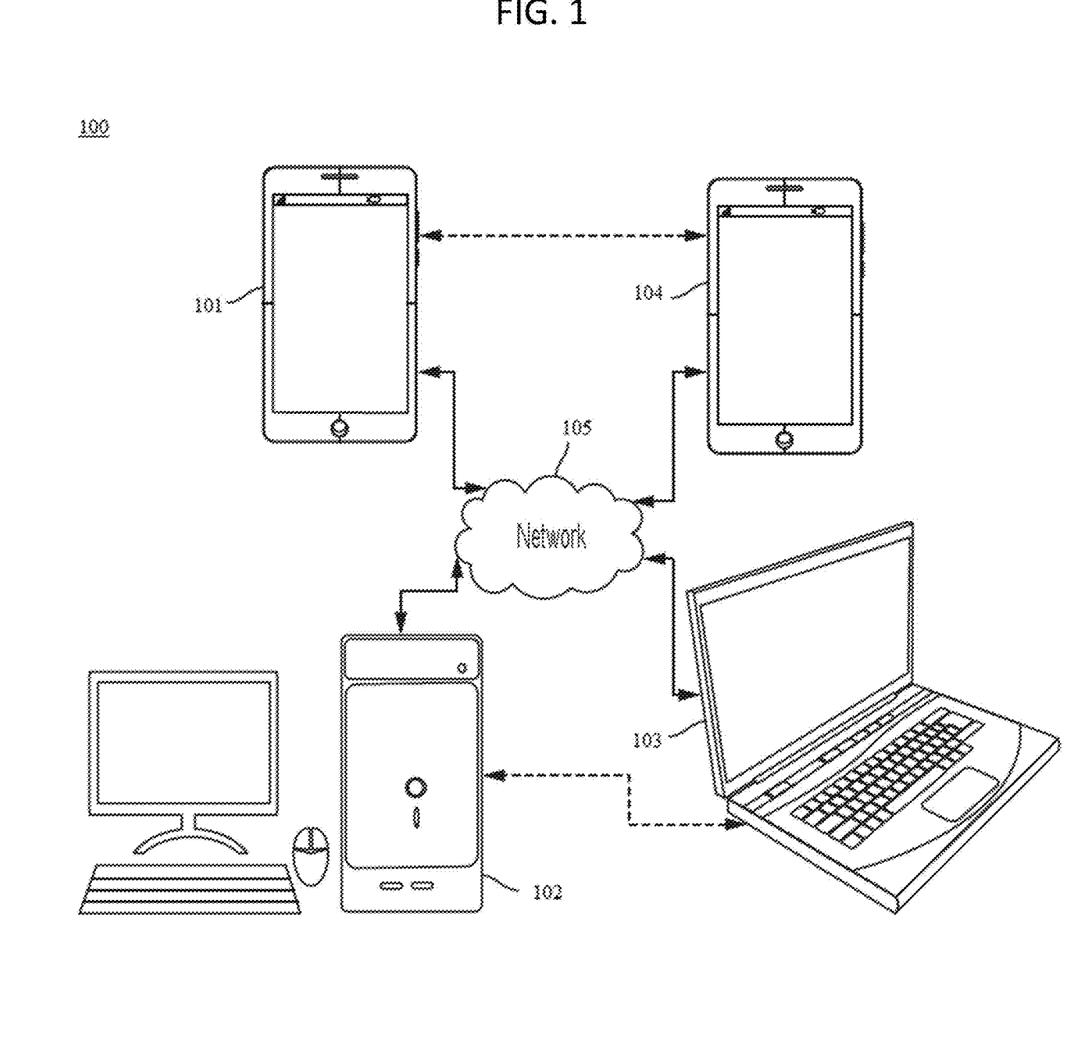
FIG. 1-4 are schematic illustrations of simplified block diagrams of a system in accordance with embodiments.

FIG. 1 is an illustration of a simplified block diagram of a system 100 in accordance with an embodiment.

The proposed features discussed below may be used separately or combined in any order. Further, the embodiments may be implemented by processing circuitry (e.g., one or more processors or one or more integrated circuits). In one example, the one or more processors execute a program that is stored in a non-transitory computer-readable medium.

FIG. 1 illustrates a simplified block diagram of a communication system 100 according to an embodiment of the present disclosure. The communication system 100 may include at least two terminals 102 and 103 interconnected via a network 105. For unidirectional transmission of data, a first terminal 103 may code video data at a local location for transmission to the other terminal 102 via the network 105. The second terminal 102 may receive the coded video data of the other terminal from the network 105, decode the coded data and display the recovered video data. Unidirectional data transmission may be common in media serving applications and the like.

FIG. 1 illustrates a second pair of terminals 101 and 104 provided to support bidirectional transmission of coded video that may occur, for example, during videoconferencing. For bidirectional transmission of data, each terminal 101 and 104 may code video data captured at a local location for transmission to the other terminal via the network 105. Each terminal 101 and 104 also may receive the coded video data transmitted by the other terminal, may decode the coded data and may display the recovered video data at a local display device.

In FIG. 1, the terminals 101, 102, 103 and 104 may be illustrated as servers, personal computers and smart phones but the principles of the present disclosure are not so limited. The terminals 101, 102, 103, and 104 may be individually capable of capturing images and videos, such as with devices further described with FIGS. 2 and 9 for example, utilized in embodiments described herein. Embodiments of the present disclosure find application with laptop computers, tablet computers, media players and/or dedicated video conferencing equipment. The network 105 represents any number of networks that convey coded video data among the terminals 101, 102, 103 and 104, including for example wireline and/or wireless communication networks. The communication network 105 may exchange data in circuit-switched and/or packet-switched channels. Representative networks include telecommunications networks, local area networks, wide area networks and/or the Internet. For the purposes of the present discussion, the architecture and topology of the network 105 may be immaterial to the operation of the present disclosure unless explained herein below.

Figure 2:
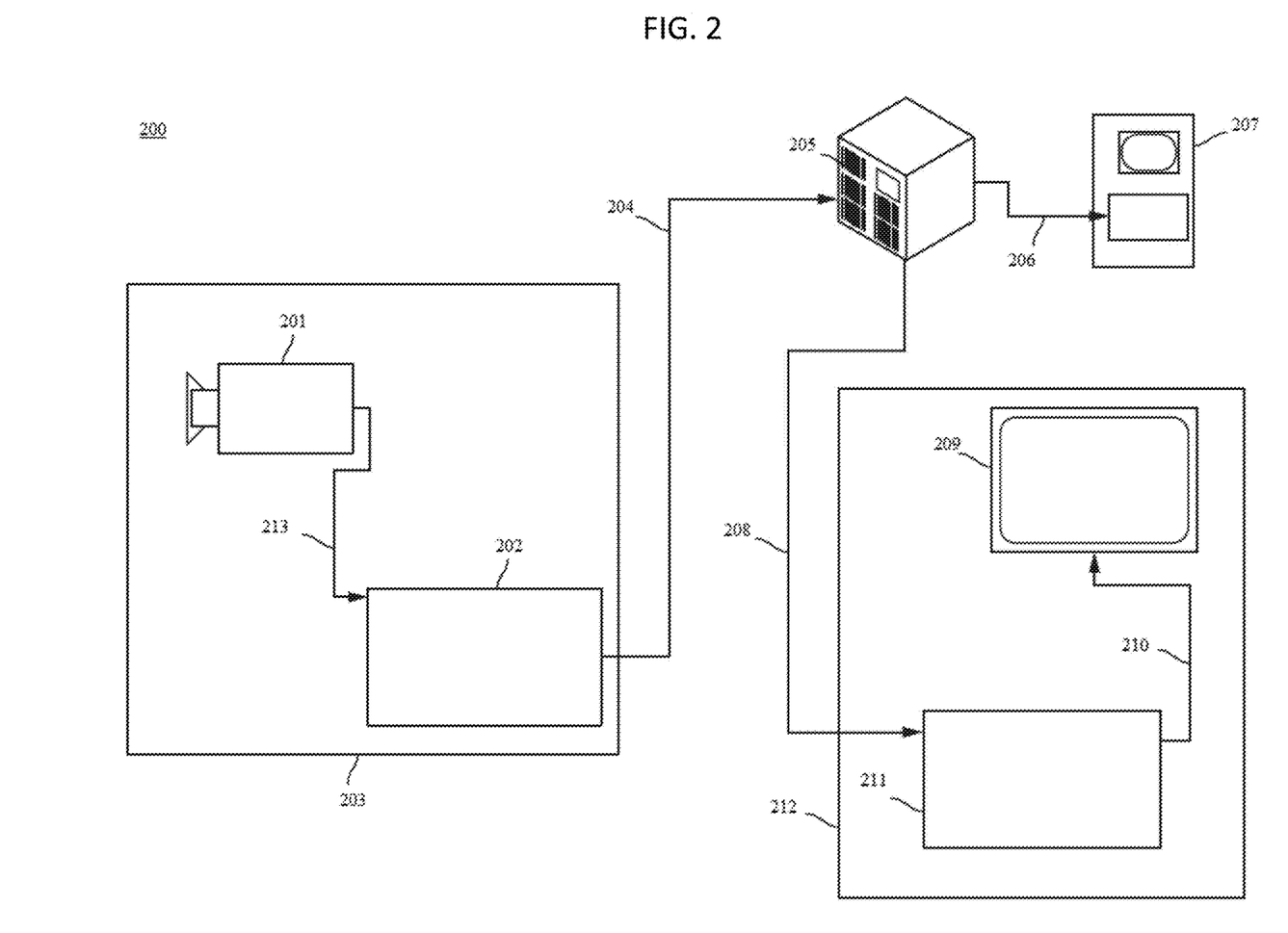

FIG. 2 illustrates, as an example for an application for the disclosed subject matter, the placement of a video encoder and decoder in a streaming environment. The disclosed subject matter can be equally applicable to other video enabled applications, including, for example, video conferencing, digital TV, storing of compressed video on digital media including CD, DVD, memory stick and the like, and so on.

A streaming system may include a capture subsystem 203 that can include a video source 201, for example a digital camera, creating, for example, an uncompressed video sample stream 213. That sample stream 213, depicted as a bold line to emphasize a high data volume when compared to encoded video bitstreams, can be processed by an encoder 202 coupled to the camera 201. The encoder 202 can include hardware, software, or a combination thereof to enable or implement aspects of the disclosed subject matter as described in more detail below. The encoded video bitstream 204, depicted as a thin line to emphasize the lower data volume when compared to the sample stream, can be stored on a streaming server 205 for future use. One or more streaming clients 212 and 207 can access the streaming server 205 to retrieve copies 208 and 206 of the encoded video bitstream 204. A client 212 can include a video decoder 211 which decodes the incoming copy of the encoded video bitstream 208 and creates an outgoing video sample stream 210 that can be rendered on a display 209 or other rendering device (not depicted). In some streaming systems, the video bitstreams 204, 206 and 208 can be encoded according to certain video coding/compression standards. Examples of those standards are noted above and described further herein.

Figure 3:
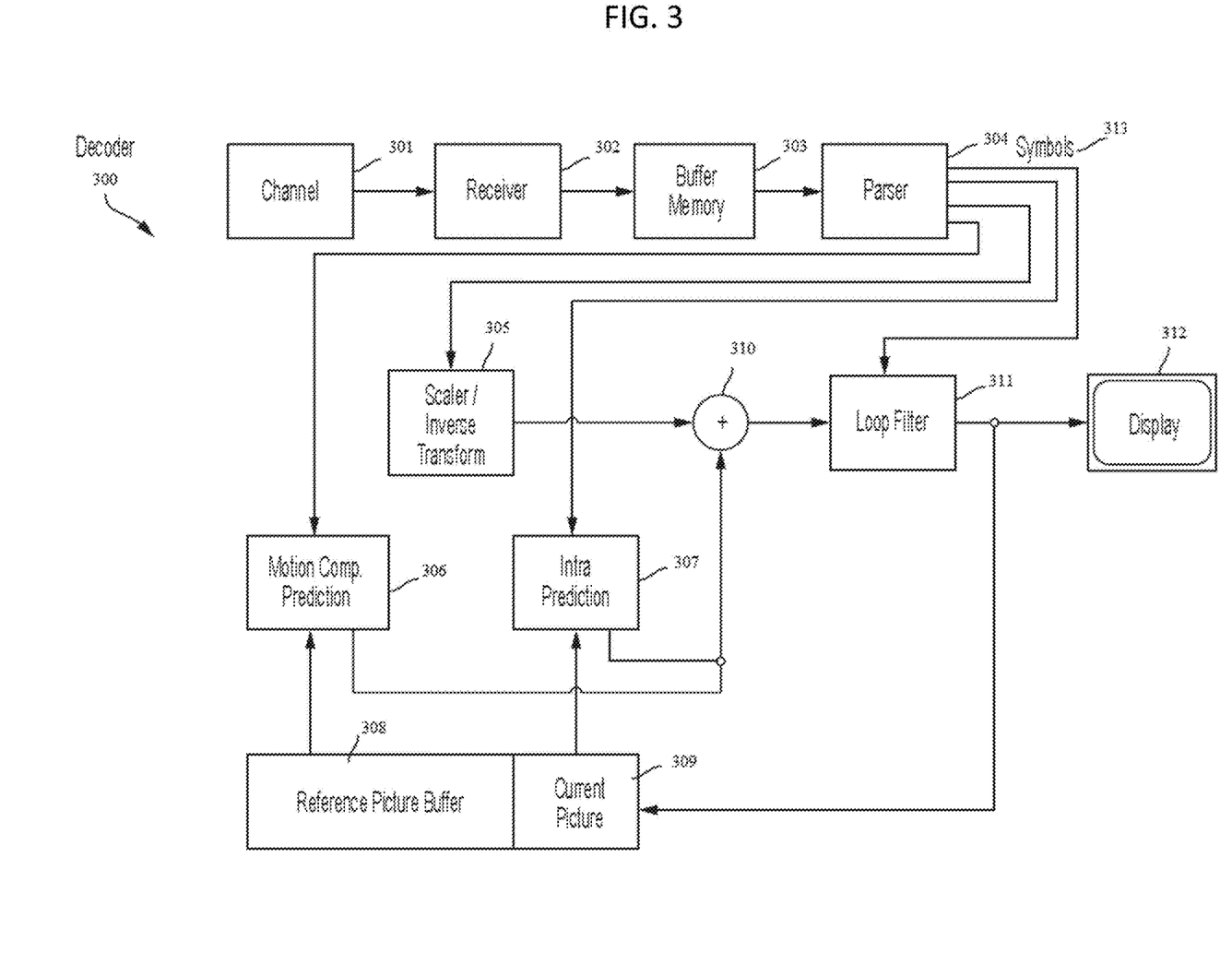

FIG. 3 may be a functional block diagram of a video decoder 300 according to an embodiment of the present invention.

A receiver 302 may receive one or more codec video sequences to be decoded by the decoder 300; in the same or another embodiment, one coded video sequence at a time, where the decoding of each coded video sequence is independent from other coded video sequences. The coded video sequence may be received from a channel 301, which may be a hardware/software link to a storage device which stores the encoded video data. The receiver 302 may receive the encoded video data with other data, for example, coded audio data and/or ancillary data streams, that may be forwarded to their respective using entities (not depicted). The receiver 302 may separate the coded video sequence from the other data. To combat network jitter, a buffer memory 303 may be coupled in between receiver 302 and entropy decoder/parser 304 ("parser" henceforth). When receiver 302 is receiving data from a store/forward device of sufficient bandwidth and controllability, or from an isosychronous network, the buffer 303 may not be needed, or can be small. For use on best effort packet networks such as the Internet, the buffer 303 may be required, can be comparatively large and can advantageously of adaptive size.

The video decoder 300 may include a parser 304 to reconstruct symbols 313 from the entropy coded video sequence. Categories of those symbols include information used to manage operation of the decoder 300, and potentially information to control a rendering device such as a display 312 that is not an integral part of the decoder but can be coupled to it. The control information for the rendering device(s) may be in the form of Supplementary Enhancement Information (SEI messages) or Video Usability Information (VUI) parameter set fragments (not depicted). The parser 304 may parse/entropy-decode the coded video sequence received. The coding of the coded video sequence can be in accordance with a video coding technology or standard, and can follow principles well known to a person skilled in the art, including variable length coding, Huffman coding, arithmetic coding with or without context sensitivity, and so forth. The parser 304 may extract from the coded video sequence, a set of subgroup parameters for at least one of the subgroups of pixels in the video decoder, based upon at least one parameters corresponding to the group. Subgroups can include Groups of Pictures (GOPs), pictures, tiles, slices, macroblocks, Coding Units (CUs), blocks, Transform Units (TUs), Prediction Units (PUs) and so forth. The entropy decoder/parser may also extract from the coded video sequence information such as transform coefficients, quantizer parameter values, motion vectors, and so forth.

The parser 304 may perform entropy decoding/parsing operation on the video sequence received from the buffer 303, so to create symbols 313. The parser 304 may receive encoded data, and selectively decode particular symbols 313. Further, the parser 304 may determine whether the particular symbols 313 are to be provided to a Motion Compensation Prediction unit 306, a scaler/inverse transform unit 305, an Intra Prediction Unit 307, or a loop filter 311.

Reconstruction of the symbols 313 can involve multiple different units depending on the type of the coded video picture or parts thereof (such as: inter and intra picture, inter and intra block), and other factors. Which units are involved, and how, can be controlled by the subgroup control information that was parsed from the coded video sequence by the parser 304. The flow of such subgroup control information between the parser 304 and the multiple units below is not depicted for clarity.

Beyond the functional blocks already mentioned, decoder 200 can be conceptually subdivided into a number of functional units as described below. In a practical implementation operating under commercial constraints, many of these units interact closely with each other and can, at least partly, be integrated into each other. However, for the purpose of describing the disclosed subject matter, the conceptual subdivision into the functional units below is appropriate.

A first unit is the scaler/inverse transform unit 305. The scaler/inverse transform unit 305 receives quantized transform coefficient as well as control information, including which transform to use, block size, quantization factor, quantization scaling matrices, etc. as symbol(s) 313 from the parser 304. It can output blocks comprising sample values, that can be input into aggregator 310.

In some cases, the output samples of the scaler/inverse transform 305 can pertain to an intra coded block; that is: a block that is not using predictive information from previously reconstructed pictures, but can use predictive information from previously reconstructed parts of the current picture. Such predictive information can be provided by an intra picture prediction unit 307. In some cases, the ultra picture prediction unit 307 generates a block of the same size and shape of the block under reconstruction, using surrounding already reconstructed information fetched from the current (partly reconstructed) picture 309. The aggregator 310, in some cases, adds, on a per sample basis, the prediction information the intra prediction unit 307 has generated to the output sample information as provided by the scaler/inverse transform unit 305.

In other cases, the output samples of the scaler/inverse transform unit 305 can pertain to an inter coded, and potentially motion compensated block. In such a case, a Motion Compensation Prediction unit 306 can access reference picture memory 308 to fetch samples used for prediction. After motion compensating the fetched samples in accordance with the symbols 313 pertaining to the block, these samples can be added by the aggregator 310 to the output of the scaler/inverse transform unit (in this case called the residual samples or residual signal) so to generate output sample information. The addresses within the reference picture memory form where the motion compensation unit fetches prediction samples can be controlled by motion vectors, available to the motion compensation unit in the form of symbols 313 that can have, for example X, Y, and reference picture components. Motion compensation also can include interpolation of sample values as fetched from the reference picture memory when sub-sample exact motion vectors are in use, motion vector prediction mechanisms, and so forth.

The output samples of the aggregator 310 can be subject to various loop filtering techniques in the loop filter unit 311. Video compression technologies can include in-loop filter technologies that are controlled by parameters included in the coded video bitstream and made available to the loop filter unit 311 as symbols 313 from the parser 304, but can also be responsive to meta-information obtained during the decoding of previous (in decoding order) parts of the coded picture or coded video sequence, as well as responsive to previously reconstructed and loop-filtered sample values.

The output of the loop filter unit 311 can be a sample stream that can be output to the render device 312 as well as stored in the reference picture memory 557 for use in future inter-picture prediction.

Certain coded pictures, once fully reconstructed, can be used as reference pictures for future prediction. Once a coded picture is fully reconstructed and the coded picture has been identified as a reference picture (by, for example, parser 304), the current reference picture 309 can become part of the reference picture buffer 308, and a fresh current picture memory can be reallocated before commencing the reconstruction of the following coded picture.

The video decoder 300 may perform decoding operations according to a predetermined video compression technology that may be documented in a standard, such as ITU-T Rec. H.265. The coded video sequence may conform to a syntax specified by the video compression technology or standard being used, in the sense that it adheres to the syntax of the video compression technology or standard, as specified in the video compression technology document or standard and specifically in the profiles document therein. Also necessary for compliance can be that the complexity of the coded video sequence is within bounds as defined by the level of the video compression technology or standard. In some cases, levels restrict the maximum picture size, maximum frame rate, maximum reconstruction sample rate (measured in, for example megasamples per second), maximum reference picture size, and so on. Limits set by levels can, in some cases, be further restricted through Hypothetical Reference Decoder (HRD) specifications and metadata for HRD buffer management signaled in the coded video sequence.

In an embodiment, the receiver 302 may receive additional (redundant) data with the encoded video. The additional data may be included as part of the coded video sequence(s). The additional data may be used by the video decoder 300 to properly decode the data and/or to more accurately reconstruct the original video data. Additional data can be in the form of, for example, temporal, spatial, or signal-to-noise ratio (SNR) enhancement layers, redundant slices, redundant pictures, forward error correction codes, and so on.

Figure 4:
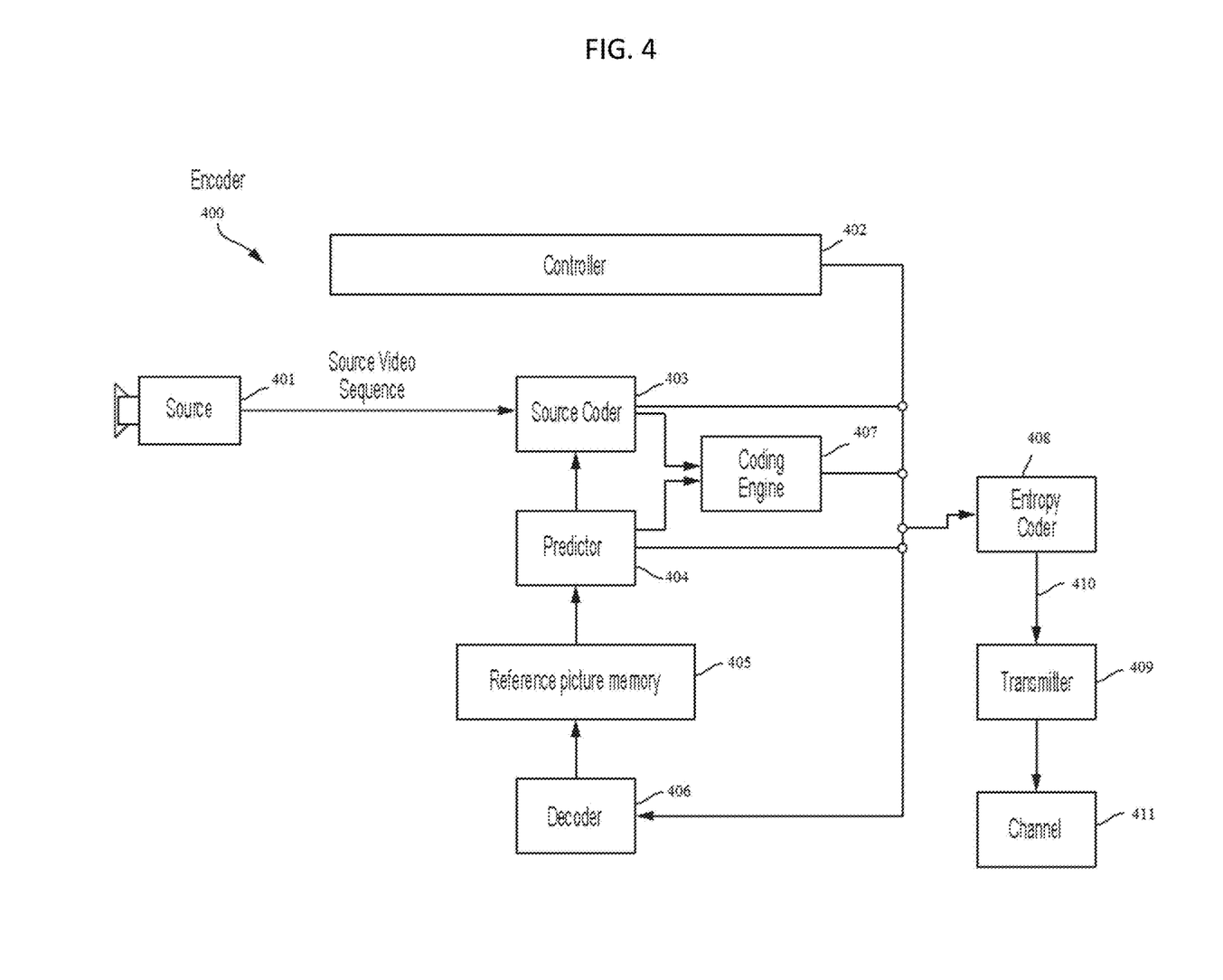

FIG. 4 may be a functional block diagram of a video encoder 400 according to an embodiment of the present disclosure.

The encoder 400 may receive video samples from a video source 401 (that is not part of the encoder) that may capture video image(s) to be coded by the encoder 400.

The video source 401 may provide the source video sequence to be coded by the encoder (303) in the form of a digital video sample stream that can be of any suitable bit depth (for example: 8 bit, 10 bit, 12 bit, . . . ), any colorspace (for example, BT.601 Y CrCB, RGB, . . . ) and any suitable sampling structure (for example Y CrCb 4:2:0, Y CrCb 4:4:4). In a media serving system, the video source 401 may be a storage device storing previously prepared video. In a videoconferencing system, the video source 401 may be a camera that captures local image information as a video sequence. Video data may be provided as a plurality of individual pictures that impart motion when viewed in sequence. The pictures themselves may be organized as a spatial array of pixels, wherein each pixel can comprise one or more samples depending on the sampling structure, color space, etc. in use. A person skilled in the art can readily understand the relationship between pixels and samples. The description below focuses on samples.

According to an embodiment, the encoder 400 may code and compress the pictures of the source video sequence into a coded video sequence 410 in real time or under any other time constraints as required by the application. Enforcing appropriate coding speed is one function of Controller 402. Controller controls other functional units as described below and is functionally coupled to these units. The coupling is not depicted for clarity. Parameters set by controller can include rate control related parameters (picture skip, quantizer, lambda value of rate-distortion optimization techniques, . . . ), picture size, group of pictures (GOP) layout, maximum motion vector search range, and so forth. A person skilled in the art can readily identify other functions of controller 402 as they may pertain to video encoder 400 optimized for a certain system design.

Some video encoders operate in what a person skilled in the art readily recognizes as a "coding loop." As a simplified description, a coding loop can consist of the encoding part of an encoder 402 ("source coder" henceforth) (responsible for creating symbols based on an input picture to be coded, and a reference picture(s)), and a (local) decoder 406 embedded in the encoder 400 that reconstructs the symbols to create the sample data that a (remote) decoder also would create (as any compression between symbols and coded video bitstream is lossless in the video compression technologies considered in the disclosed subject matter). That reconstructed sample stream is input to the reference picture memory 405. As the decoding of a symbol stream leads to bit-exact results independent of decoder location (local or remote), the reference picture buffer content is also bit exact between local encoder and remote encoder. In other words, the prediction part of an encoder "sees" as reference picture samples exactly the same sample values as a decoder would "see" when using prediction during decoding. This fundamental principle of reference picture synchronicity (and resulting drift, if synchronicity cannot be maintained, for example because of channel errors) is well known to a person skilled in the art.

The operation of the "local" decoder 406 can be the same as of a "remote" decoder 300, which has already been described in detail above in conjunction with FIG. 3. Briefly referring also to FIG. 4, however, as symbols are available and en/decoding of symbols to a coded video sequence by entropy coder 408 and parser 304 can be lossless, the entropy decoding parts of decoder 300, including channel 301, receiver 302, buffer 303, and parser 304 may not be fully implemented in local decoder 406.

An observation that can be made at this point is that any decoder technology except the parsing/entropy decoding that is present in a decoder also necessarily needs to be present, in substantially identical functional form, in a corresponding encoder. The description of encoder technologies can be abbreviated as they are the inverse of the comprehensively described decoder technologies. Only in certain areas a more detail description is required and provided below.

As part of its operation, the source coder 403 may perform motion compensated predictive coding, which codes an input frame predictively with reference to one or more previously-coded frames from the video sequence that were designated as "reference frames." In this manner, the coding engine 407 codes differences between pixel blocks of an input frame and pixel blocks of reference frame(s) that may be selected as prediction reference(s) to the input frame.

The local video decoder 406 may decode coded video data of frames that may be designated as reference frames, based on symbols created by the source coder 403. Operations of the coding engine 407 may advantageously be lossy processes. When the coded video data may be decoded at a video decoder (not shown in FIG. 4), the reconstructed video sequence typically may be a replica of the source video sequence with some errors. The local video decoder 406 replicates decoding processes that may be performed by the video decoder on reference frames and may cause reconstructed reference frames to be stored in the reference picture cache 405. In this manner, the encoder 400 may store copies of reconstructed reference frames locally that have common content as the reconstructed reference frames that will be obtained by a far-end video decoder (absent transmission errors).

The predictor 404 may perform prediction searches for the coding engine 407. That is, for a new frame to be coded, the predictor 404 may search the reference picture memory 405 for sample data (as candidate reference pixel blocks) or certain metadata such as reference picture motion vectors, block shapes, and so on, that may serve as an appropriate prediction reference for the new pictures. The predictor 404 may operate on a sample block-by-pixel block basis to find appropriate prediction references. In some cases, as determined by search results obtained by the predictor 404, an input picture may have prediction references drawn from multiple reference pictures stored in the reference picture memory 405.

The controller 402 may manage coding operations of the video coder 403, including, for example, setting of parameters and subgroup parameters used for encoding the video data.

Output of all aforementioned functional units may be subjected to entropy coding in the entropy coder 408. The entropy coder translates the symbols as generated by the various functional units into a coded video sequence, by loss-less compressing the symbols according to technologies known to a person skilled in the art as, for example Huffman coding, variable length coding, arithmetic coding, and so forth.

The transmitter 409 may buffer the coded video sequence(s) as created by the entropy coder 408 to prepare it for transmission via a communication channel 411, which may be a hardware/software link to a storage device which would store the encoded video data. The transmitter 409 may merge coded video data from the video coder 403 with other data to be transmitted, for example, coded audio data and/or ancillary data streams (sources not shown).

The controller 402 may manage operation of the encoder 400. During coding, the controller 405 may assign to each coded picture a certain coded picture type, which may affect the coding techniques that may be applied to the respective picture. For example, pictures often may be assigned as one of the following frame types:

An Intra Picture (I picture) may be one that may be coded and decoded without using any other frame in the sequence as a source of prediction. Some video codecs allow for different types of Intra pictures, including, for example Independent Decoder Refresh Pictures. A person skilled in the art is aware of those variants of I pictures and their respective applications and features.

A Predictive picture (P picture) may be one that may be coded and decoded using intra prediction or inter prediction using at most one motion vector and reference index to predict the sample values of each block.

A Bi-directionally Predictive Picture (B Picture) may be one that may be coded and decoded using intra prediction or inter prediction using at most two motion vectors and reference indices to predict the sample values of each block. Similarly, multiple-predictive pictures can use more than two reference pictures and associated metadata for the reconstruction of a single block.

Source pictures commonly may be subdivided spatially into a plurality of sample blocks (for example, blocks of 4×4, 8×8, 4×8, or 16×16 samples each) and coded on a block-by-block basis. Blocks may be coded predictively with reference to other (already coded) blocks as determined by the coding assignment applied to the blocks' respective pictures. For example, blocks of I pictures may be coded non-predictively or they may be coded predictively with reference to already coded blocks of the same picture (spatial prediction or intra prediction). Pixel blocks of P pictures may be coded non-predictively, via spatial prediction or via temporal prediction with reference to one previously coded reference pictures. Blocks of B pictures may be coded non-predictively, via spatial prediction or via temporal prediction with reference to one or two previously coded reference pictures.

The video coder 400 may perform coding operations according to a predetermined video coding technology or standard, such as ITU-T Rec. H.265. In its operation, the video coder 400 may perform various compression operations, including predictive coding operations that exploit temporal and spatial redundancies in the input video sequence. The coded video data, therefore, may conform to a syntax specified by the video coding technology or standard being used.

In an embodiment, the transmitter 409 may transmit additional data with the encoded video. The video coder 403 may include such data as part of the coded video sequence. Additional data may comprise temporal/spatial/SNR enhancement layers, other forms of redundant data such as redundant pictures and slices, Supplementary Enhancement Information (SEI) messages, Visual Usability Information (VUI) parameter set fragments, and so on.

Figure 5:
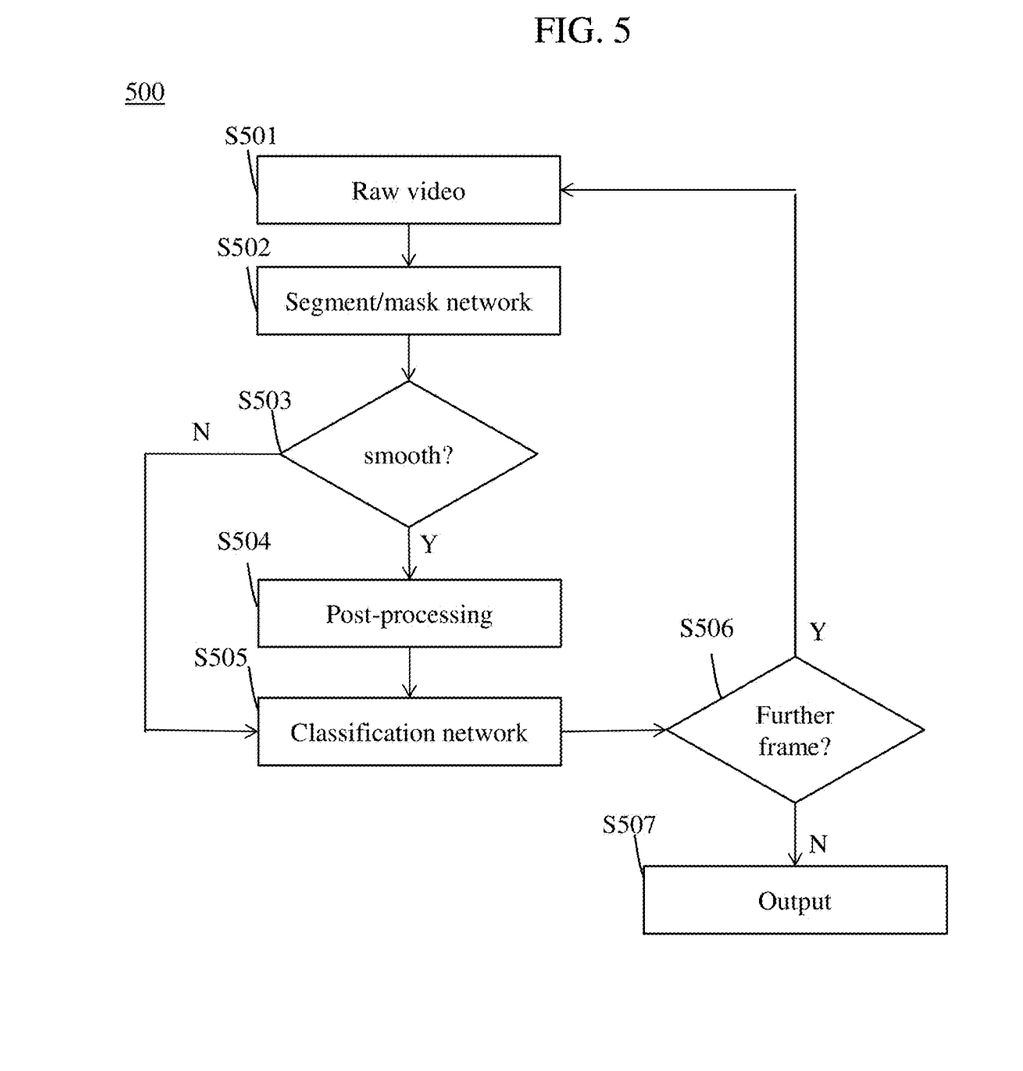
FIG. 5 is a flowchart illustrating features according to embodiments.

FIG. 5 illustrates a flowchart 500 according to exemplary embodiments.

At S 501, a raw image or video signal is obtained, and at S502 that information is fed into a segmentation network for object segmentation. According to embodiments, a UNet segmentation network is employed, and that network may be trained via manually labeled masks. For example, during training, a set of data augmentation techniques may be used, such as: histogram equalization, Gaussian blurring, rotation with different angles, and zoom in and zoom out.

As a goal of the segmentation network may be to achieve background and illumination invariance of a possibly noisy input raw image or video signal, and it may be determined whether a threshold level of background and/or illumination invariance has been achieved, and if so, then the process may proceed to S503. Further, segmenting the input image may also remove various features of the hand and instead result simply in a mask having a hand region and a blank region outside of the hand region. One of ordinary skill in the art would recognize such features as a technical improvement avoiding such inter/intra observer imprecision described above.

Figure 6:
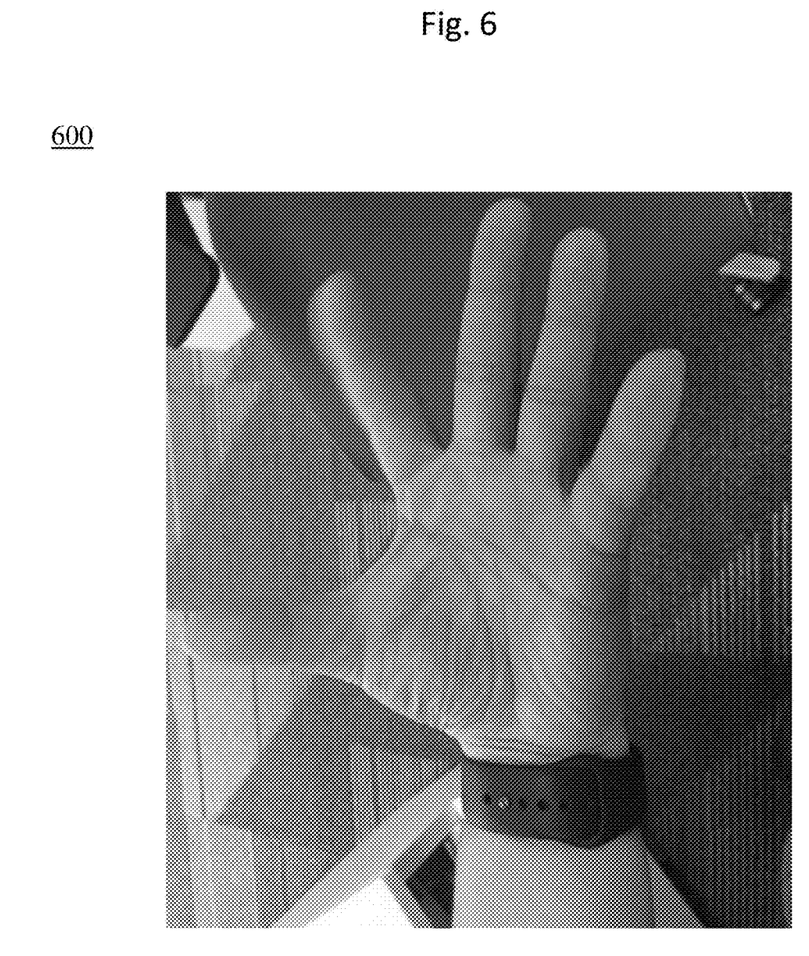
FIGS. 6-8 are illustrations of images according to embodiments.
Figure 7:
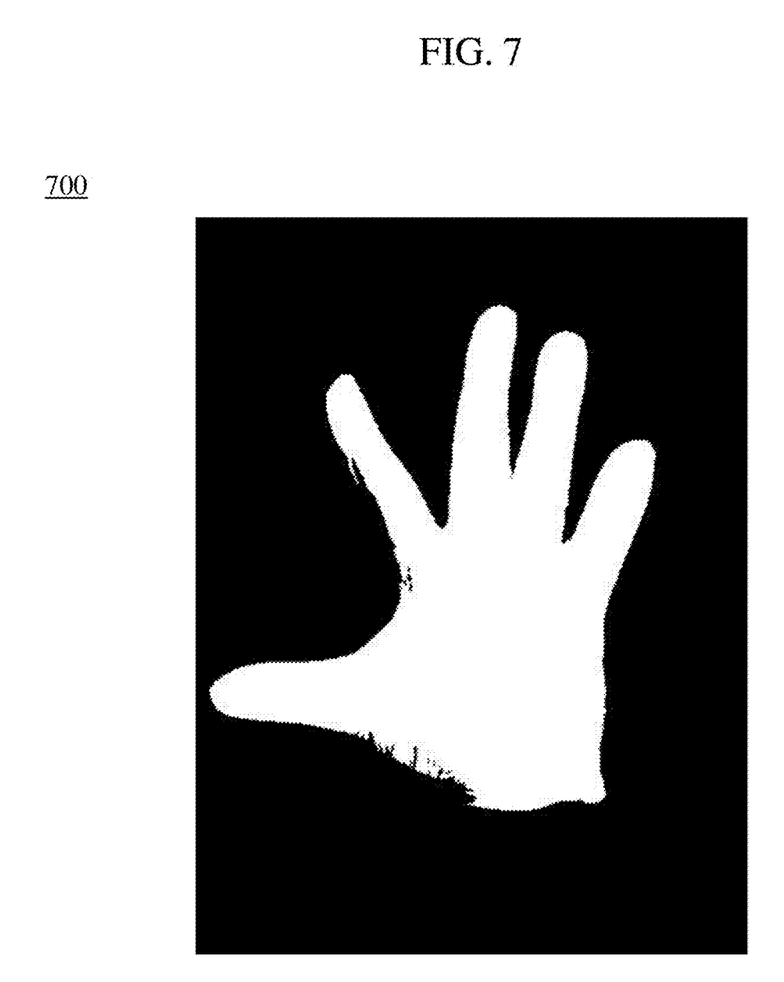

FIG. 6 illustrates an image 600 which includes various background features in addition to a hand. As the illumination may vary and portions of the background may be moving and therefore interfering with the analysis of any hand dyskinesias, the segmentation network at S502 may remove that background and instead yield a mask, such as with the image 700 in FIG. 7, in which the background is removed and any illumination may be removed by virtue of the masking processes. However, as illustrated in FIG. 7, the image 700 may not be entirely smooth.

Therefore, at S503 it may be determined whether the output of S502 contains a smooth image. For example, feature detection such as edge detection may be utilized to detect smoothness. If further smoothing is determined to be necessary, then at S505 the image 700 of FIG. 7 may be post-processed into the smoother image 800 of FIG. 8 to obtain a smooth border.

At S505, the image 800 may be fed into a 3D CNN classification network for activity recognition. The classification network may be trained to detect various markers according to the UPDRS using AI technology. That is, rather than feeding a raw video image into the classification network, the hand mask is segmented and fed into the classification network thereby avoiding challenges caused by different backgrounds and illuminations.

At S506 it may be determined whether further image data is to be input and analyzed, and if so, then the process returns to S501. Otherwise, the process may proceed to S507 where a result of the classification may be any of displayed by a display, output according to a sound or speech, and stored in a memory or database at a local or networked location. The result may include information about what information was determined about any dyskinesias in the hand.

According to exemplary embodiments, one or more hands may be analyzed per input image.

According to exemplary embodiments ones of the features in FIG. 5 may be rearranged. For example, the S503 and S506 may be removed. In a case where the S506 is removed, the output at S507 may automatically be output before the system checks whether further information is to be input, and in a case where the smoothing and post-processing is omitted, a result of the segmentation may be directly added to the classification network at S505 for example.

Figure 8:
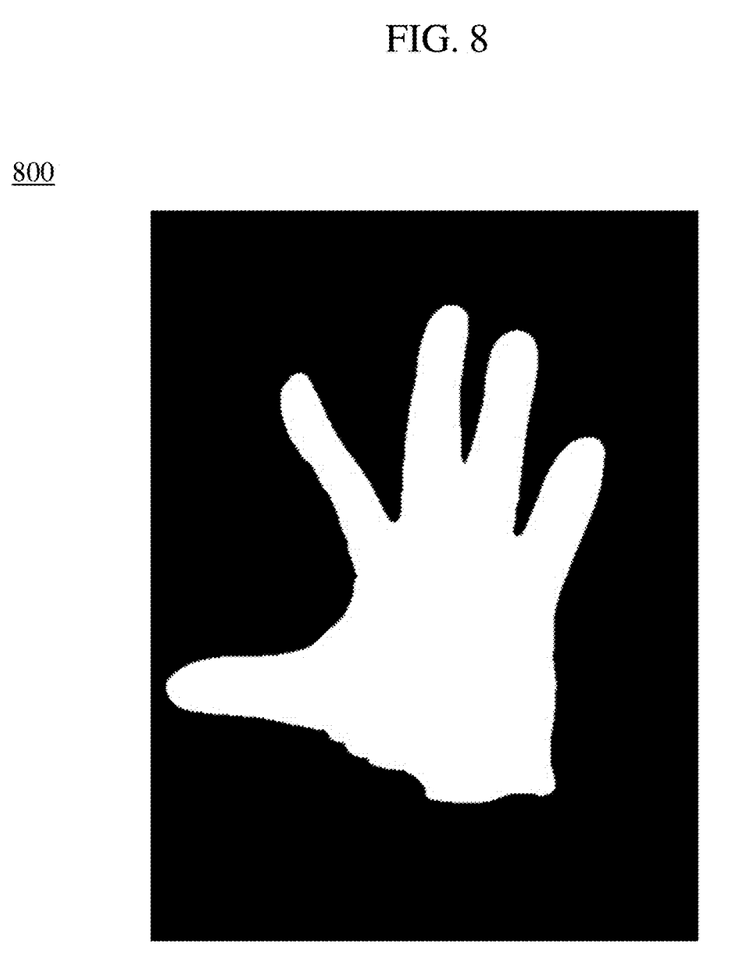

Further, as the image 700 and the image 800 may be masks of the hand from the image 600, the image 700 and 800 may have various features such as finger and palm prints removed thereby further simplifying processing of the segmented image according to embodiments.

Embodiments have been evaluated on a UCF101 and Sports1M dataset with inputs thereto as raw video and as hand masks fed into these networks to predict a current state of the hand activity. By using the hand masks, the classification networks may handle the simplified inputs as invariant to background and illumination changes of the raw video data.

Classifications may include determining poses which include whether a tremor is absent, slight, moderate, severe, or marked according to the UPDRS. The poses also may include various hand movements, finger tappings, rigidity, and rapid alternating movements such as pronation-supination movements of the hands, vertically and horizontally, and/or both hands simultaneously may similarly be classified. Various sequences of input images may be analyzed together by first segmenting those images and then post-processing the segmented images, as described above, to determine the various poses across multiple of the input images.

The techniques described above, can be implemented as computer software using computer-readable instructions and physically stored in one or more computer-readable media or by a specifically configured one or more hardware processors. For example, FIG. 9 shows a computer system 900 suitable for implementing certain embodiments of the disclosed subject matter.

The computer software can be coded using any suitable machine code or computer language, that may be subject to assembly, compilation, linking, or like mechanisms to create code comprising instructions that can be executed directly, or through interpretation, micro-code execution, and the like, by computer central processing units (CPUs), Graphics Processing Units (GPUs), and the like.

The instructions can be executed on various types of computers or components thereof, including, for example, personal computers, tablet computers, servers, smartphones, gaming devices, internet of things devices, and the like.

Figure 9:
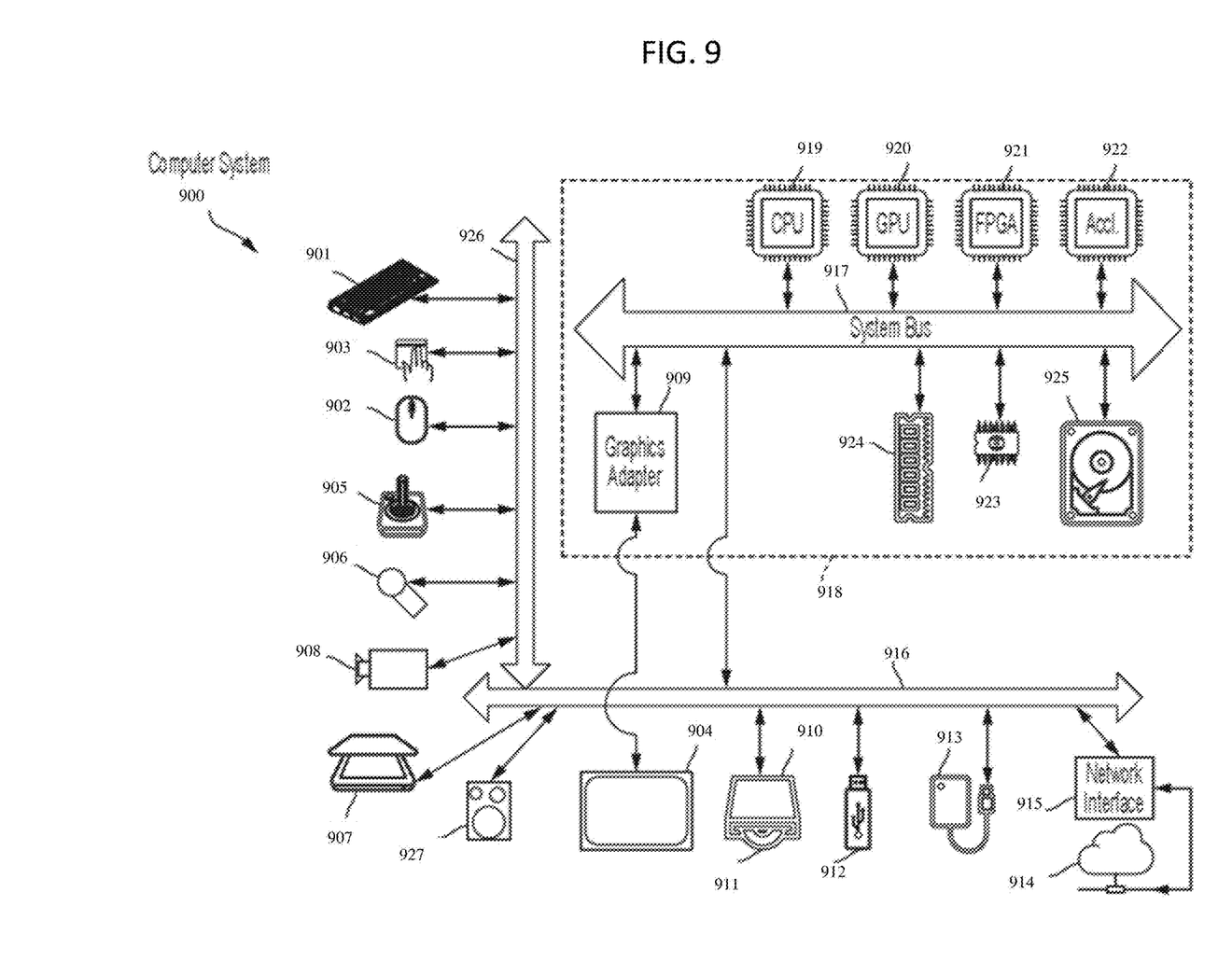
FIG. 9 is a schematic illustration of a simplified block diagram of a system in accordance with embodiments.

The components shown in FIG. 9 for computer system 900 are exemplary in nature and are not intended to suggest any limitation as to the scope of use or functionality of the computer software implementing embodiments of the present disclosure. Neither should the configuration of components be interpreted as having any dependency or requirement relating to any one or combination of components illustrated in the exemplary embodiment of a computer system 900.

Computer system 900 may include certain human interface input devices. Such a human interface input device may be responsive to input by one or more human users through, for example, tactile input (such as: keystrokes, swipes, data glove movements), audio input (such as: voice, clapping), visual input (such as: gestures), olfactory input (not depicted). The human interface devices can also be used to capture certain media not necessarily directly related to conscious input by a human, such as audio (such as: speech, music, ambient sound), images (such as: scanned images, photographic images obtain from a still image camera), video (such as two-dimensional video, three-dimensional video including stereoscopic video).

Input human interface devices may include one or more of (only one of each depicted): keyboard 901, mouse 902, trackpad 903, touch screen 904, joystick 905, microphone 906, scanner 907, camera 908.

Computer system 900 may also include certain human interface output devices. Such human interface output devices may be stimulating the senses of one or more human users through, for example, tactile output, sound, light, and smell/taste. Such human interface output devices may include tactile output devices (for example tactile feedback by the touch-screen 904, or joystick 1405, but there can also be tactile feedback devices that do not serve as input devices), audio output devices (such as: speakers 927, headphones (not depicted)), visual output devices such as screens 904, possibly connected via a graphics adapter 909, to include CRT screens, LCD screens, plasma screens, OLED screens, each with or without touch-screen input capability, each with or without tactile feedback capability—some of which may be capable to output two dimensional visual output or more than three dimensional output through means such as stereographic output; virtual-reality glasses (not depicted), holographic displays and smoke tanks (not depicted)), and printers (not depicted).

Computer system 900 can also include human accessible storage devices and their associated media such as optical media including CD/DVD ROM/RW 910 with CD/DVD 911 or the like media, thumb-drive 912, removable hard drive or solid state drive 913, legacy magnetic media such as tape and floppy disc (not depicted), specialized ROM/ASIC/PLD based devices such as security dongles (not depicted), and the like.

Those skilled in the art should also understand that term "computer readable media" as used in connection with the presently disclosed subject matter does not encompass transmission media, carrier waves, or other transitory signals.

Computer system 900 can also include interface to one or more communication networks 914. Networks 914 can for example be wireless, wireline, optical. Networks 914 can further be local, wide-area, metropolitan, vehicular and industrial, real-time, delay-tolerant, and so on. Examples of networks 914 include local area networks such as Ethernet, wireless LANs, cellular networks to include GSM, 3G, 4G, 5G, LTE and the like, TV wireline or wireless wide area digital networks to include cable TV, satellite TV, and terrestrial broadcast TV, vehicular and industrial to include CANBus, and so forth. Certain networks 914 commonly require external network interface adapters 915 that attached to certain general-purpose data ports or peripheral buses 916 (such as, for example USB ports of the computer system 900; others are commonly integrated into the core of the computer system 900 by attachment to a system bus 917 as described below (for example Ethernet interface into a PC computer system or cellular network interface into a smartphone computer system). Using any of these networks, computer system 900 can communicate with other entities. Such communication can be uni-directional, receive only (for example, broadcast TV), uni-directional send-only (for example CANbusto certain CANbus devices), or bi-directional, for example to other computer systems using local or wide area digital networks. Certain protocols and protocol stacks can be used on each of those networks 914 and network interfaces 915 as described above.

Aforementioned human interface devices, human-accessible storage devices, and network interfaces 915 can be attached to a core 918 of the computer system 900.

The core 918 can include one or more Central Processing Units (CPU) 919, Graphics Processing Units (GPU) 920, specialized programmable processing units in the form of Field Programmable Gate Areas (FPGA) 921, hardware accelerators 922 for certain tasks, and so forth. These devices, along with Read-only memory (ROM) 923, Random-access memory 924, internal mass storage 925 such as internal non-user accessible hard drives, SSDs, and the like, may be connected through a system bus 917. In some computer systems, the system bus 917 can be accessible in the form of one or more physical plugs to enable extensions by additional CPUs, GPU, and the like. The peripheral devices can be attached either directly to the core's system bus 917, or through a peripheral bus 926. Architectures for a peripheral bus include PCI, USB, and the like.

CPUs 919, GPUs 920 FPGAs 921, and accelerators 922 can execute certain instructions that, in combination, can make up the aforementioned computer code. That computer code can be stored in ROM 923 or RAM 924. Transitional data can also be stored in RAM 924, whereas permanent data can be stored for example, in the internal mass storage 925. Fast storage and retrieve to any of the memory devices can be enabled through the use of cache memory, that can be closely associated with one or more CPU 919, GPU 920, mass storage 925, ROM 923, RAM 924, and the like.

The computer readable media can have computer code thereon for performing various computer-implemented operations. The media and computer code can be those specially designed and constructed for the purposes of the present disclosure, or they can be of the kind well known and available to those having skill in the computer software arts.

As an example and not by way of limitation, the computer system having architecture 900, and specifically the core 918 can provide functionality as a result of processor(s) (including CPUs, GPUs, FPGA, accelerators, and the like) executing software embodied in one or more tangible, computer-readable media. Such computer-readable media can be media associated with user-accessible mass storage as introduced above, as well as certain storage of the core 918 that are of non-transitory nature, such as core-internal mass storage 925 or ROM 923. The software implementing various embodiments of the present disclosure can be stored in such devices and executed by core 918. A computer-readable medium can include one or more memory devices or chips, according to particular needs. The software can cause the core 918 and specifically the processors therein (including CPU, GPU, FPGA, and the like) to execute particular processes or particular parts of particular processes described herein, including defining data structures stored in RAM 924 and modifying such data structures according to the processes defined by the software. In addition or as an alternative, the computer system can provide functionality as a result of logic hardwired or otherwise embodied in a circuit (for example: accelerator 922), which can operate in place of or together with software to execute particular processes or particular parts of particular processes described herein. Reference to software can encompass logic, and vice versa, where appropriate. Reference to a computer-readable media can encompass a circuit (such as an integrated circuit (IC)) storing software for execution, a circuit embodying logic for execution, or both, where appropriate. The present disclosure encompasses any suitable combination of hardware and software.

While this disclosure has described several exemplary embodiments, there are alterations, permutations, and various substitute equivalents, which fall within the scope of the disclosure. It will thus be appreciated that those skilled in the art will be able to devise numerous systems and methods which, although not explicitly shown or described herein, embody the principles of the disclosure and are thus within the spirit and scope thereof.

Besides the mentioned design and procedure of the proposed framework, there are several alternatives:

The extraction module may use a combination of several algorithms and structures, for instance, RNN with CNN, RNN with a support vector machine (SVM), etc. Since the flexibility of definition of "feature" in machine learning, the exact implementation of extraction modules may vary as would be recognized from this application.

For feature extraction modules, similar models could share a subset of parameters to account the similarity among inputs.

According to embodiments, the framework may be designed as an end-to-end procedure that the whole framework will be optimized and altered simultaneously according to exemplary embodiments, and an alternative may be a step-by-step training procedure, in which extraction modules can be trained separately, for instance, using encoder and decoder structure, according to other embodiments.

This approach can be extended to other applications which have multiple sources of inputs.

Further, there may be, based on the extraction modules and analysis tasks selected to apply with, optional feedback mechanisms added from an output to the feature extraction modules of the features described herein. For instance, in an RNN model for multi-symptom diagnosis, according to exemplary embodiments, such feedback mechanisms may further account for dependencies among symptoms, and a feedback link can be added for other diagnosed symptoms to inform one or more extraction modules and one or more of their attention mechanisms how and where to concentrate or focus in subsequent steps.

While this disclosure has described several exemplary embodiments, there are alterations, permutations, and various substitute equivalents, which fall within the scope of the disclosure. It will thus be appreciated that those skilled in the art will be able to devise numerous systems and methods which, although not explicitly shown or described herein, embody the principles of the disclosure and are thus within the spirit and scope thereof

What is claimed is:

1. An apparatus comprising:
    at least one memory configured to store computer program code; and
    at least one hardware processor configured to access said computer program code and operate as instructed by said computer program code, said computer program code including:
        image segmentation code configured to cause the at least one hardware processor to segment an image of a person's hand from an input image by extracting the person's hand from the input image such that an illuminance is removed from the input image;
        determining code configured to cause the at least one hardware processor to determine that a threshold level of illuminance is removed in the segmented image from the input image to achieve illumination invariance;
        post processing code configured to cause the at least one hardware processor to smooth at least one edge of the person's hand in the segmented image in response to determining that the threshold level of illuminance is removed in the segmented image from the input image; and
        classification code configured to cause the at least one processor to classify the segmented image in which the at least one edge has been smoothed according to at least one predefined pose comprising a hand tremor.

2. The apparatus according to claim 1, wherein the at least one predefined pose further comprises any of a finger tapping and a pronation-supination movement of the person's hand.

3. The apparatus according to claim 1, wherein the image segmentation code is further configured to cause the at least one hardware processor to segment the image of the person's hand by extracting the person's hand from the input image such that a background, other than the person's hand, is removed from the input image.

4. The apparatus according to claim 1, wherein the segmented image comprises a mask of the person's hand from the input image such that a background of the input image and an illuminance of the input image are removed from the input image.

5. The apparatus according to claim 1, wherein the image segmentation code is further configured to cause the at least one hardware processor to segment the image according to a UNet segmentation network.

6. The apparatus according to claim 5, wherein the UNet segmentation network comprises data trained by manually labeled masks and at least one set of data augmentation techniques including any of histogram equalization, Gaussian blurring, rotation, and zoom techniques.

7. The apparatus according to claim 5, wherein the classification code is further configured to cause the at least one hardware processor to classify the segmented image according to a convolutional neural network (CNN).

8. The apparatus according to claim 1, wherein the classification code is further configured to cause the at least one hardware processor to classify the segmented image according to a convolutional neural network (CNN).

9. A method performed by at least one hardware processor, the method comprising:
- segmenting an image of a person's hand from an input image by extracting the person's hand from the input image such that an illuminance is removed from the input image;
- determining that a threshold level of illuminance is removed in the segmented image from the input image to achieve illumination invariance;
- smoothing at least one edge of the person's hand in the segmented image in response to determining that the threshold level of illuminance is removed in the segmented image from the input image; and
- classifying the segmented image in which the at least one edge has been smoothed according to at least one predefined pose comprising a hand tremor.

10. The method according to claim 9, wherein the at least one predefined pose further comprises any of a finger tapping and a pronation-supination movement of the person's hand.

11. The method according to claim 9, wherein segmenting the image of the person's hand further comprises extracting the person's hand from the input image such that a background, other than the person's hand, is removed from the input image.

12. The method according to claim 9, wherein the segmented image comprises a mask of the person's hand from the input image such that a background of the input image and an illuminance of the input image are removed from the input image.

13. The method according to claim 9, wherein segmenting the image comprises segmenting the image according to a UNet segmentation network.

14. The method according to claim 13, wherein the UNet segmentation network comprises data trained by manually labeled masks and at least one set of data augmentation techniques including any of histogram equalization, Gaussian blurring, rotation, and zoom techniques.

15. The method according to claim 13, wherein classifying the segmented image comprises classifying the segmented image according to a convolutional neural network (CNN).

16. A non-transitory computer readable medium storing a program causing a computer to execute a process, the process comprising:
- segmenting an image of a person's hand from an input image by extracting the person's hand from the input image such that an illuminance is removed from the input image;
- determine that a threshold level of illuminance is removed in the segmented image from the input image to achieve illumination invariance;
- smoothing at least one edge of the person's hand in the segmented image in response to determining that the threshold level of illuminance is removed in the segmented image from the input image; and
- classifying the segmented image in which the at least one edge has been smoothed according to at least one predefined pose comprising a hand tremor.

* * * * *